United States Patent [19]

Eakins et al.

[11] 4,190,673
[45] Feb. 26, 1980

[54] COLCHICINE OPHTHALMIC COMPOSITION AND METHOD OF USE

[75] Inventors: Kenneth E. Eakins, Sparkill; Parimal Bhattacherjee, Nyack, both of N.Y.

[73] Assignee: Nelson Research & Development Company, Irvine, Calif.

[21] Appl. No.: 904,586

[22] Filed: May 10, 1978

[51] Int. Cl.$^2$ .............................................. A61K 31/165
[52] U.S. Cl. ..................................................... 424/324
[58] Field of Search .......................................... 424/324

[56] References Cited

U.S. PATENT DOCUMENTS 3,641,146  2/1972  Lettre et al. .......................... 424/324

FOREIGN PATENT DOCUMENTS 4685  1/1967  France ....................................... 424/324

OTHER PUBLICATIONS

Chem. Abst. 43, 7568(c), (1949), Estable.
Chem. Abst. 56, 66128(d) (1962)—Mugler et al.
Chem. Abst. 70, 27484(t) (1969)—Malawista et al.
Chem. Abst. 75, 108337(c) (1971)—Akinosho et al.

Primary Examiner—Douglas W. Robinson
Attorney, Agent, or Firm—Martin A. Voet

[57] ABSTRACT

A therapeutic composition comprising a topically administrable ophthalmic pharmaceutical carrier and colchicine. The foregoing composition temporarily alleviates the symptoms of glaucoma when topically administered to the eye.

8 Claims, No Drawings

COLCHICINE OPHTHALMIC COMPOSITION AND METHOD OF USE

BACKGROUND OF THE INVENTION

1. Field of the Invention

The invention relates generally to a composition and method for reducing intraocular pressure (IOP) in humans and animals. More particular, the invention relates to a method for temporarily alleviating the symptoms of glaucoma.

2. Background of the Prior Art

Colchicine is a major alkaloid of *Colchicum autumnale L., Libaceoe* whose extraction procedure is well-known in the art. Colchicine has been used heretofore in research on plant genetics and in the therapeutic treatment of gout and Familial Mediterranean Fever.

Glaucoma is a condition of the eye characterized by increased intraocular pressure. Untreated, the condition eventually leads to irreversible retinal damage and blindness. Conventional therapy for glaucoma is with pilocarpine and/or epinephrine administered topically several times daily.

One of the problems with many conventional drugs for the treatment of glaucoma is that they decrease the size of the pupil, i.e., they are miotic drugs. This is an undesirable side effect, resulting in temporarily impaired vision.

SUMMARY OF THE INVENTION

There has now been discovered a method of reducing IOP and for treating glaucoma in which there is a minimum of miotic side effects.

The present invention relates to a therapeutic composition comprising a topically administrable ophthalmic pharmaceutical carrier and an effective amount of colchicine.

The present invention also relates to a method for temporarily alleviating the symptoms of glaucoma in humans comprising topically administering to the eyes of a human having glaucoma an effective amount of the foregoing composition.

DESCRIPTION OF THE INVENTION

Suitable ophthalmic carriers are known to those skilled in the art and all such conventional carriers may be employed in the present invention. Thus, a particular carrier may take the form of a sterile, ophthalmic ointment, cream, gel, solution, or dispersion. Also included in suitable ophthalmic carriers are slow release polymers, e.g., "Ocusert" polymers, "Hydron" polymers, etc. Stabilizers may also be used such as, for example, chelating agents, e.g., EDTA. Antioxidants may also be used, e.g., sodium bisulfite, sodium thiosulfite, 8-hydroxy quinoline or ascorbic acid. Sterility typically will be maintained by conventional ophthalmic preservatives, e.g., chlorbutanol, benzalkonium chloride, cetylpyridium chloride, phenyl mercuric salts, thimerosal, etc., for aqueous formulations, and used in amounts which are nontoxic and which generally vary from about 0.001 to about 0.1% by weight of the aqueous solution. Conventional preservatives for ointments include methyl and propyl parabens. Typical ointment bases include white petrolatum and mineral oil or liquid petrolatum. However, preserved aqueous carriers are preferred. Solutions may be manually delivered to the eye in suitable dosage form, e.g., eye drops, or delivered by suitable microdrop or spray apparatus typically affording a metered dose of medicament. Examples of suitable ophthalmic carriers include sterile, substantially isotonic, aqueous solutions containing minor amounts, i.e., less than about 5% by weight hydroxypropylmethylcellulose, polyvinyl alcohol, carboxymethylcellulose, hydroxyethylcellulose, glycerine and EDTA. The solutions are preferably maintained at substantially neutral pH and isotonic with appropriate amounts of conventional buffers, e.g., phosphate, borate, acetate, tris, etc.

A preferred ophthalmic composition is a preserved aqueous solution containing the following ingredients at the indicated concentration.

| | | |
|---|---|---|
| Colchicine | Wt. percent | 1 |
| Stabilizer | " | 0.01 |
| Preservative | " | 0.005 |
| Buffer | M | 0.05 |
| NaCl q.s. ad isotonic. | | |
| Water q.s. ad 100 percent. | | |

The amount of colchicine to be used in the therapeutic treatment of glaucoma will vary with the age of the patient and the severity of the glaucoma. Generally a dose level of one or two drops of the foregoing aqueous solution 1–4 times daily would be a suitable dosage amount. Generally, the concentration of colchicine will vary between about 0.01 and about 5 and preferably between about 0.1 and 2%.

EXAMPLE I

A study on the effect of topical administration of colchicine on rabbit intraocular pressure was performed. Different concentrations of colchicine in phosphate buffer, pH 7.5 were instilled onto the cornea of the test eye of New Zealand white rabbits at time 0, the control eye received an equal volume of the phosphate buffer without colchicine. IOP was measured with a pneumatic tonometer and is shown as the difference between the test and control eyes. Five animals were used for each concentration. The results are shown in Table 1 below:

Table 1

| Concentration of Colchicine (%) | Change in IOP (mmHg) | | | | |
|---|---|---|---|---|---|
| | 0 | 8 hrs | 24 hrs | 48 hrs | 72 hrs |
| 0.05 | 0 | −0.5 | −3 | 0 | — |
| 0.1 | 0 | −0.5 | −4 | −1.5 | — |
| 0.5 | 0 | −1 | −9 | −3 | −0.5 |
| 2.0 | 0 | +2.5 | −9 | −6 | −4 |

The highest concentration of colchicine (2%) resulted in an initial rise in IOP, while the remaining concentrations produced a lowering of IOP without the initial rise in pressure. The lowest concentration of colchicine (0.05%) showed no ocular irritation or miosis, while the remaining concentrations showed mild ocular irritation and a slight, transient pupillary constriction. The fall in IOP at all doses was slow in onset, becoming apparent 8 hours after administration, reaching a maximum by 24 hours and then slowly returning to normal.

I claim:

1. A method for reducing intraocular pressure in humans and animals comprising topically administering to the eye of a human or animal having increased intraocular pressure an effective, intraocular pressure reducing amount of Colchicine together with a suitable ophthalmic pharmaceutical carrier.

2. The method of claim 1 wherein the carrier is an aqueous solution additionally containing a preservative.

3. The method of claim 1 wherein an effective amount of Colchicine is between about 0.01% and about 5%.

4. The method of claim 1 wherein an effective amount of Colchicine is between about 0.1% and 2%.

5. A method for treating glaucoma in humans comprising topically administering to the eye of a human having glaucoma an effective, intraocular pressure reducing amount of Colchicine together with a suitable ophthalmic carrier.

6. The method of claim 5 wherein the carrier is an aqueous solution additionally containing a preservative.

7. The method of claim 5 wherein an effective amount of Colchicine is between about 0.01% and 5%.

8. The method of claim 5 wherein an effective amount of Colchicine is between about 0.1% and 2%.

* * * * *